United States Patent
Kim et al.

(10) Patent No.: US 8,882,667 B2
(45) Date of Patent: Nov. 11, 2014

(54) ACCESSORIES FOR REMOTE MONITORING

(75) Inventors: Jong Pal Kim, Seoul (KR); Kun Soo Shin, Seongnam-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1836 days.

(21) Appl. No.: 11/436,769

(22) Filed: May 19, 2006

(65) Prior Publication Data
US 2007/0106145 A1 May 10, 2007

(30) Foreign Application Priority Data
Oct. 11, 2005 (KR) ........................ 10-2005-0095644

(51) Int. Cl.
*A61B 5/00* (2006.01)
*H01Q 1/48* (2006.01)
*H01Q 1/40* (2006.01)
*A61B 5/0205* (2006.01)
*A61B 5/04* (2006.01)

(52) U.S. Cl.
CPC .............. *A61B 5/0205* (2013.01); *A61B 5/441* (2013.01); *A61B 5/04004* (2013.01); *A61B 5/0002* (2013.01)
USPC ............................ 600/301; 343/846; 343/873

(58) Field of Classification Search
USPC ............. 600/300, 549; 340/539.1; 348/218.1
See application file for complete search history.

(56) References Cited

U.S. PATENT DOCUMENTS

| | | | | |
|---|---|---|---|---|
| 5,057,106 A | * | 10/1991 | Kasevich et al. | 606/33 |
| 5,136,303 A | * | 8/1992 | Cho et al. | 343/718 |
| 5,159,347 A | * | 10/1992 | Osterwalder | 343/787 |
| 5,600,307 A | * | 2/1997 | Aslan | 340/600 |
| 6,018,325 A | * | 1/2000 | Lundgren | 343/890 |
| 6,128,528 A | * | 10/2000 | Ericksen et al. | 607/2 |
| 6,132,371 A | * | 10/2000 | Dempsey et al. | 600/300 |
| 6,366,250 B1 | * | 4/2002 | McConnell | 343/718 |
| 6,379,300 B1 | * | 4/2002 | Haubrich | 600/300 |
| 6,547,745 B1 | | 4/2003 | Rubinstein | |

(Continued)

FOREIGN PATENT DOCUMENTS

| | | |
|---|---|---|
| JP | 10-314133 | 12/1998 |
| JP | 11-188013 | 7/1999 |

(Continued)

OTHER PUBLICATIONS

Pages 48-50; "Introduction to RF Propagation", John S. Seybold, 2005.*

(Continued)

*Primary Examiner* — William Thomson
*Assistant Examiner* — Shirley Jian
(74) *Attorney, Agent, or Firm* — Staas & Halsey LLP

(57) ABSTRACT

An accessory for remote monitoring, including: a body capable of being placed on a human body; a measurement unit installed in the body and measuring a change in surroundings; a signal processing unit for processing a signal acquired from the measurement unit; and a wireless communication unit including a monopole antenna transmitting the signal processed by the signal processing unit and a ground installed along the body, corresponding to the monopole antenna. The signal processing unit and the monopole antenna are manufactured in a small size to be formed in the accessories body or periphery of the accessories body, and a space for wiring the ground may be obtained by using a band or the accessories body in an extended shape.

12 Claims, 5 Drawing Sheets

(56) References Cited

U.S. PATENT DOCUMENTS

| | | | |
|---|---|---|---|
| 6,590,541 B1* | 7/2003 | Schultze | 343/741 |
| 6,685,634 B1 | 2/2004 | Fry | 600/300 |
| 6,788,199 B2* | 9/2004 | Crabtree et al. | 340/539.13 |
| 6,804,561 B2* | 10/2004 | Stover | 607/60 |
| 6,809,701 B2* | 10/2004 | Amundson et al. | 343/873 |
| 6,856,131 B2* | 2/2005 | Miyazawa et al. | 324/252 |
| 7,075,455 B2* | 7/2006 | Nishimura et al. | 340/870.28 |
| 7,095,372 B2* | 8/2006 | Soler Castany et al. | 343/700 MS |
| 7,196,666 B2* | 3/2007 | Allen et al. | 343/700 MS |
| 7,220,220 B2* | 5/2007 | Stubbs et al. | 482/72 |
| 7,277,125 B2* | 10/2007 | Nishimura et al. | 348/218.1 |
| 7,289,855 B2* | 10/2007 | Nghiem et al. | 607/60 |
| 7,346,312 B2* | 3/2008 | Irazoqui-Pastor et al. | 455/41.2 |
| 7,782,269 B2* | 8/2010 | Soler Castany et al. | 343/846 |
| 7,903,043 B2* | 3/2011 | Rawat et al. | 343/873 |
| 2002/0126057 A1* | 9/2002 | King et al. | 343/725 |
| 2003/0034887 A1* | 2/2003 | Crabtree et al. | 340/539 |
| 2003/0097302 A1* | 5/2003 | Overhultz et al. | 705/14 |
| 2004/0005889 A1* | 1/2004 | Nishimura et al. | 455/423 |
| 2004/0027306 A1* | 2/2004 | Amundson et al. | 343/873 |
| 2004/0165076 A1* | 8/2004 | Nishimura et al. | 348/211.2 |
| 2005/0001728 A1* | 1/2005 | Appelt et al. | 340/573.1 |
| 2005/0110687 A1* | 5/2005 | Starkie et al. | 343/700 MS |
| 2005/0134520 A1* | 6/2005 | Rawat et al. | 343/873 |
| 2006/0009702 A1* | 1/2006 | Iwaki et al. | 600/520 |
| 2006/0033664 A1* | 2/2006 | Soler Castany et al. | 343/700 MS |
| 2006/0077107 A1* | 4/2006 | Kim | 343/702 |
| 2006/0247712 A1* | 11/2006 | Fuller et al. | 607/32 |
| 2007/0066361 A1* | 3/2007 | Knudsen et al. | 455/562.1 |
| 2007/0252773 A1* | 11/2007 | Soler Castany et al. | 343/846 |
| 2008/0111678 A1* | 5/2008 | Mizoguchi et al. | 340/539.11 |

FOREIGN PATENT DOCUMENTS

| | | |
|---|---|---|
| JP | 2002-200051 | 7/2002 |
| KR | 1999-0065818 | 8/1999 |
| KR | 20-0209351 | 10/2000 |
| KR | 10-2002-0080763 | 10/2002 |
| KR | 10-2004-0050261 | 6/2004 |
| KR | 1020040072553 | 8/2004 |
| WO | WO95/28128 | 10/1995 |

OTHER PUBLICATIONS

λ/4 printed monopole antenna for 2.45GHz by Nordic Semiconductor, Jan. 21, 2005 (PDF attached).*

* cited by examiner

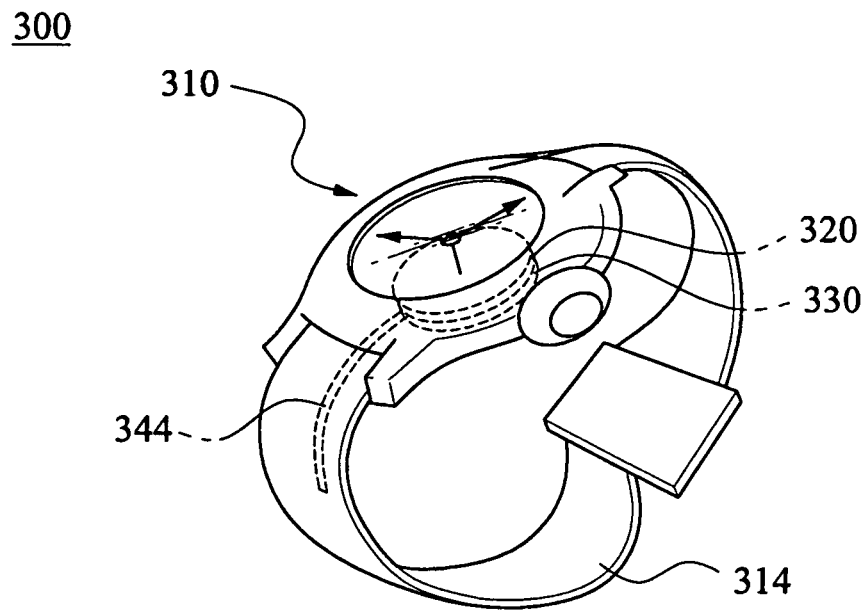
FIG. 8
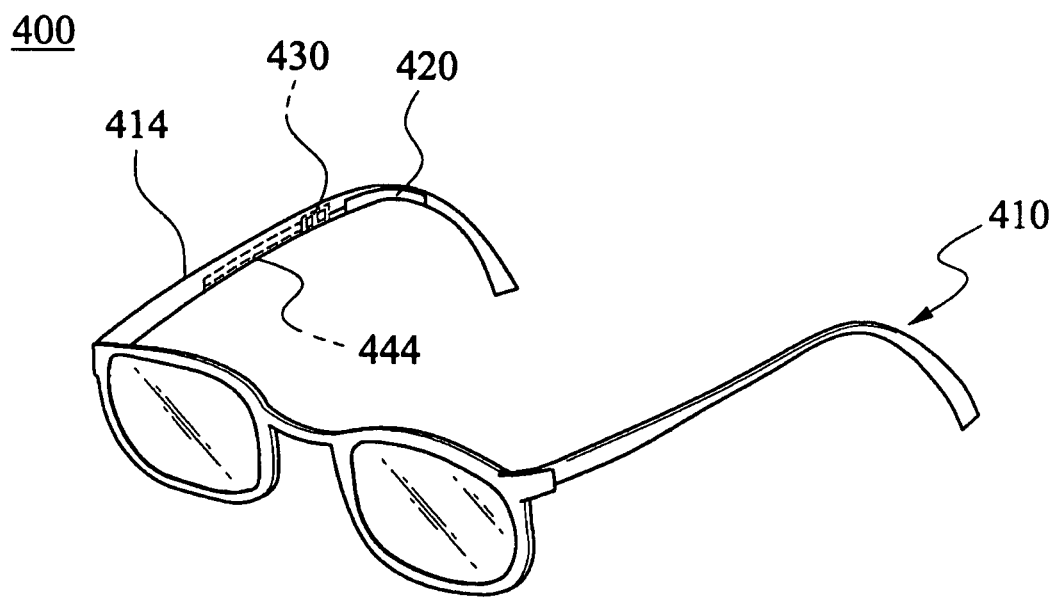

ACCESSORIES FOR REMOTE MONITORING

CROSS-REFERENCE TO RELATED APPLICATION

This application claims the benefit of Korean Patent Application No. 10-2005-0095644, filed on Oct. 11, 2005, in the Korean Intellectual Property Office, the disclosure of which is incorporated herein by reference.

BACKGROUND OF THE INVENTION

1. Field of the Invention

The present invention relates to a health care technology for measuring and monitoring a change in a body, and more particularly, relates to accessories placed on a body of a user to measure a change in the body of the user or condition of the user and communicate with an external apparatus.

2. Description of Related Art

A ubiquitous system indicates an information communication environment in which a user is unaware of a network or a computer and whose position is irrelevant while the user freely access the network. When a ubiquitous system is generally used, every one can use information technology in varied embodiments. Thus, a user could, for example, not only use such technology in a house or vehicle but also on the top of a mountain. Also, since the general use of a ubiquitous system increases the number of users of computers connected to a network, the information technology industry may be also expanded to a size and range in relation to the number of the users. Due to merits of not only portability and convenience, as described above, but also accessing a network in which time and position are irrelevant, technologies associated with Ubiquitous system are being developed in nations worldwide.

The described technologies associated with ubiquitous systems may be applied in every field of human life, and currently, in particular, due to the well-being fad, a ubiquitous healthcare (U-healthcare) is in the spotlight as a notable technical field. U-healthcare is a ubiquitous technology in which a chip or sensor associated with medical services is integrated into any part of human life, thereby naturally providing medical services to everyone at anytime and anywhere. According to the U-healthcare, medical treatments performed in only hospitals, such as various medical examinations, management of diseases, emergency care, and consulting with doctors, may be realized during everyday life.

As a result, a device capable of measuring or monitoring a change in a body or a peripheral environment may be required. Also, according to development of a technology associated with integrated circuits (IC), a circuit capable of performing desired functions may be embodied in one chip. Accordingly, according to the level of present technology, the size of a circuit unit may be minimized to several mm or less.

Also, since technology associated with antennas is continuously developed, the size of an antenna may be minimized. Generally, a small device including wireless communication function may employ a monopole antenna because the monopole antenna having a quarter (¼) length of a wavelength of a used frequency may perform efficient communication function. Also, recently, greater minimization of antennas has been made possible by employment of dielectric material or improvement of technology of antenna patterns. For example, when a monopole antenna is used for a frequency of approximately 2.45 GHz, a required length of the antenna is approximately 3 cm, and when a dielectric material or a particular pattern is used, the size of the antenna may be manufactured to be less than approximately 1 cm.

When a device for monitoring a change in a body or environments is placed on a body, a functional circuit and antenna may be minimized to a desired size. However, a ground has to have a length of ¼ wavelength, and when a monopole antenna is used in a frequency band of approximately 2.45 GHz, a required length of a ground has to be at least approximately 3 cm.

Accordingly, to manufacture a monitoring device placed on a body in a small size, since a ground of a certain length is required, there are many restrictions to manufacture the monitoring device in a micro size. Actually, when a ground is formed on a printed circuit board (PCB), as the entire size of the PCB is reduced, an area in which the ground is formed is also reduced and the antenna cannot perform its function.

BRIEF SUMMARY

An aspect of the present invention provides accessories capable of containing a circuit unit and an antenna formed in a small size and effectively providing a ground greater than a certain length.

An aspect of the present invention also provides accessories capable of being usually placed on or easily carried by using conventional small articles or accessories.

According to an aspect of the present invention, there is provided an accessory including a body capable of being placed on a human body; a measurement unit installed in the body measuring a change in surroundings; a signal processing unit processing a signal acquired from the measurement unit; and a wireless communication unit including a monopole antenna transmitting the signal processed by the signal processing unit and a ground installed along the body, corresponding to the monopole antenna.

Due to development of technology, the signal processing unit or the monopole antenna may be manufactured smaller than 1 cm. However, the ground may be required to be greater than a certain length because of resonance. Accordingly, the ground may be separately connected to a PCB substrate and wired along the accessories body, thereby manufacturing a minimized monitoring device.

The accessory may be an accessory or small article which can be placed on a human body or clothes. In detail, they may be accessories formed in the shape of a ring or other ornaments such as a necklace, a bracelet, a necktie pin and the like, and they may be small articles formed in the shape of a ring or band such as a hat, a watch, a band, a waist belt, glasses and the like. The measuring unit may be directly or indirectly in contact with the body of the user to measure an ECG, an EMG, an EEG, a GSR, a body temperature, a pulse, and a blood pressure. In addition, the measurement unit may sense temperature, pressure, humidity, components of air, composition of air, radioactivity, and deleterious bacteria of peripheral environments.

The signal processing unit for processing the measured signal may be embodied as an IC chip on the PCB substrate, and the monopole antenna may be embodied on the same. Also, the monopole antenna may be manufactured to be less than λ/4 by using high dielectric material or embodying a precision antenna pattern.

According to another aspect of the present invention, there is provided an accessory for remote monitoring, including: a body capable of being placed on an object; a measurement unit installed in the body measuring a change in a surrounding environment; a circuit unit including an integrated circuit chip processing a signal acquired from the measurement unit and a monopole antenna formed on the same substrate on which the integrated circuit chip is installed; and a ground connected to the circuit unit and extended along the body.

According to another aspect of the present invention, there is provided a method of remote monitoring, including: placing a body on the object; measuring a change in a surrounding state via a measurement unit installed in the body; processing, via a signal processing unit, a signal acquired from the measurement unit; and transmitting the signal processed by the signal processing unit via a wireless communication unit including a monopole antenna and a ground installed along the body and corresponding to the monopole antenna.

Additional and/or other aspects and advantages of the present invention will be set forth in part in the description which follows and, in part, will be obvious from the description, or may be learned by practice of the invention.

BRIEF DESCRIPTION OF THE DRAWINGS

The above and/or other aspects and advantages of the present invention will become apparent and more readily appreciated from the following detailed description, taken in conjunction with the accompanying drawings of which:

FIG. 7 is a perspective view illustrating an accessory according to still another embodiment of the present invention; and FIG. 8 is a perspective view illustrating an accessory according to yet another embodiment of the present invention.

DETAILED DESCRIPTION OF EMBODIMENTS

Figure 1:
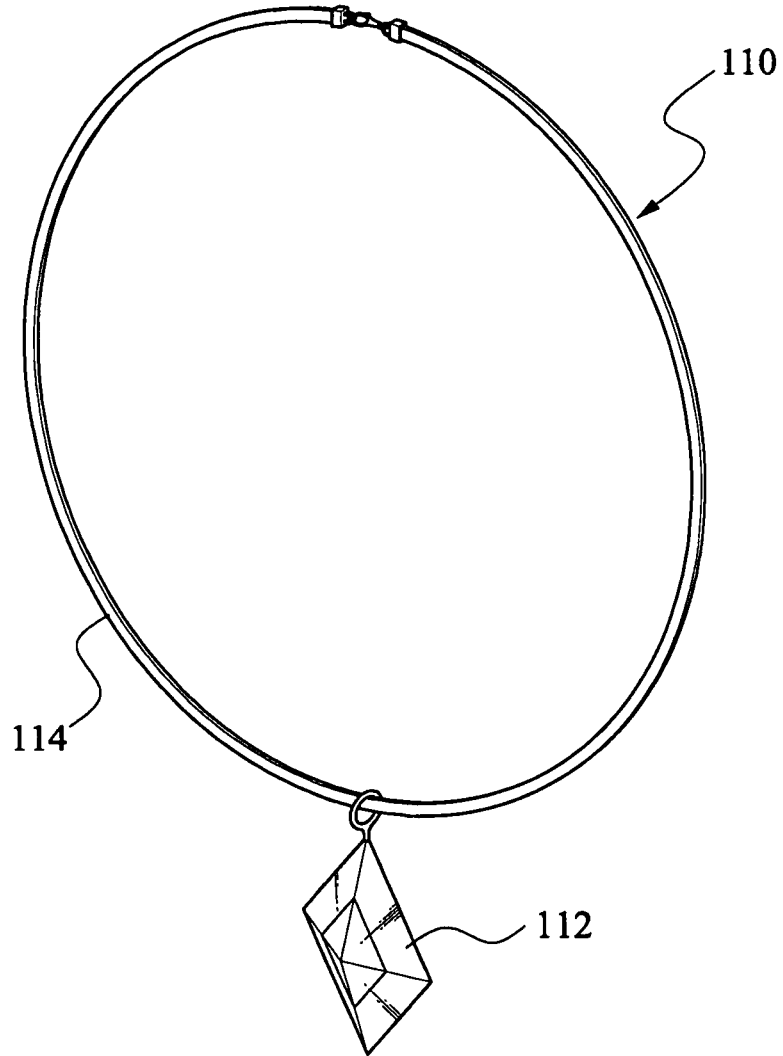
FIG. 1 is a perspective view illustrating accessories according to an embodiment of the present invention.

Reference will now be made in detail to embodiments of the present invention, examples of which are illustrated in the accompanying drawings, wherein like reference numerals refer to the like elements throughout. The embodiments are described below in order to explain the present invention by referring to the figures.

Figure 2:
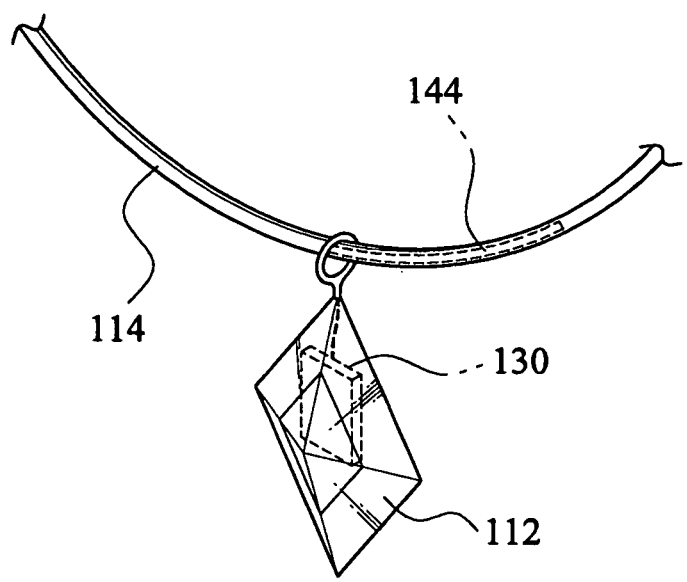
FIG. 2 is a partial enlarged front view illustrating internal elements of the an accessory of FIG. 1.
Figure 3:
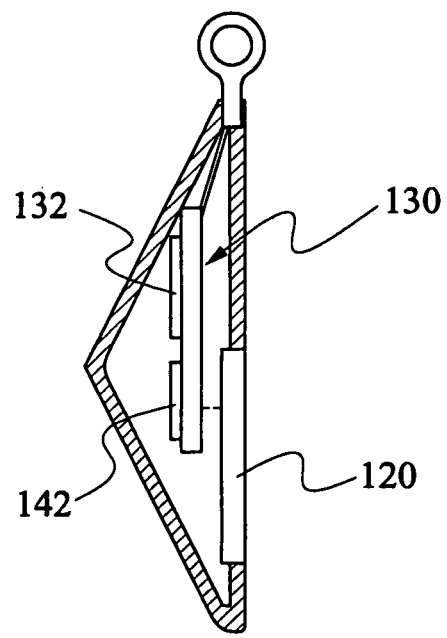
FIG. 3 is a partial enlarged cross-sectional view illustrating the internal elements of the an accessory of FIG. 1.

FIG. 1 is a perspective view illustrating an accessory according to an embodiment of the present invention, FIG. 2 is a partial enlarged front view illustrating internal elements of the accessory of FIG. 1, and FIG. 3 is a partial enlarged cross-sectional view illustrating the internal elements of the accessory of FIG. 1.

Referring to FIGS. 1 through 3, accessory 100 is a kind of necklace. Accordingly, the accessory 100 comprises an accessory body 110 in the shape of a necklace, a measurement unit 120 mounted on the accessory body 110, an IC chip 132 including a signal processing circuit, a monopole antenna 142, and a ground 144. A part of the measurement unit 120 is exposed outward to be capable of maintaining contact with the body of the user directly or indirectly.

The accessory body 110 is in the form of a general necklace and includes a pendant 112 and a necklace string 114. The measurement unit 120 that can be attached to the body is mounted on the rear side of the pendant 112, the IC chip 132 and the monopole antenna 142 are mounted on a printed circuit board (PCB) substrate 130 in the pendant 112.

The top of the pendant 112 is connected to the necklace string 114, and the monopole antenna 142 and the ground 144 are electrically connected via the engaged parts of the pendant 112 and the necklace string 114. The ground 144 is built into and along the necklace string 114 and is formed in a length of more than approximately $\lambda/4$, where the symbol of $\lambda$ indicates a wavelength of a used frequency. Accordingly, the IC chip 132 may form a wireless communication unit by using the monopole antenna 142, and the ground 144 may function as a valid image antenna with respect to the monopole antenna 142.

The measurement unit 120 installed in the pendant 112 may receive a signal for monitoring a biosignal of the user by being in contact with the body of the user. Generally, the biosignal may include an electrocardiogram, an electromyogram, an electroencephalogram, and a galvanic skin response. The measurement unit may be also used for measuring a body temperature, a pulse, or a blood pressure. In addition, the measurement unit 120 may further include other functions. In addition to the use of measuring a change in the body of a user, for example, a temperature, a pressure, a humidity, a components of air, a composition of air, a radioactivity, and a deleterious bacteria analysis of the surrounding environment may be measured. To measure environmental characteristics instead of physiological characteristics, the measurement unit may be mounted on the front of a pendant instead of the rear of the pendant.

In the present embodiment, though the measurement unit 120 includes one contact terminal, according to the type and number of biosignals to be measured, two or more contact terminals may be provided and positions of contact terminals may be determined. When a plurality of contact terminals are formed, each of the contact terminals is independently connected to the signal processing unit, and the signal processing unit may generate a signal to be transmitted to the wireless communication unit via a process of amplifying, filtering, or combining signals transmitted from each of the terminals.

Figure 4:
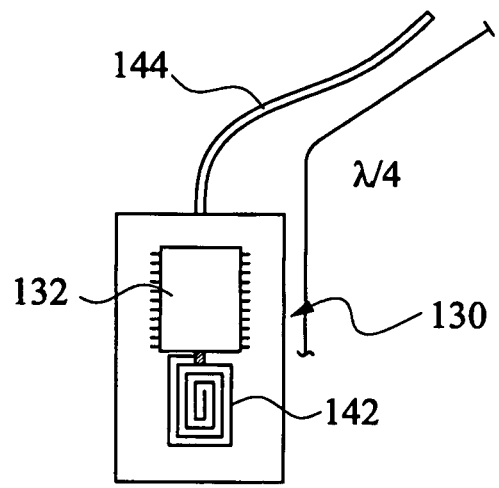
FIG. 4 is a partial enlarged front view illustrating internal elements of a pendant of the an accessory of FIG. 1.
Figure 5:
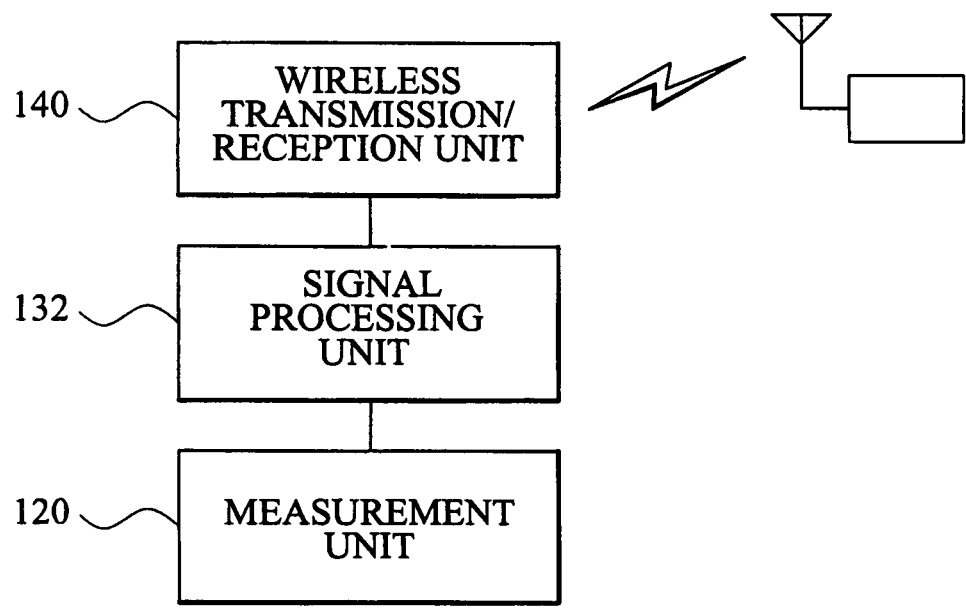
FIG. 5 is a diagram illustrating function transfer between the internal elements of FIG. 4.

FIG. 4 is a partial enlarged front view illustrating internal elements of a pendant of the accessory of FIG. 1, and FIG. 5 is a diagram illustrating function transfer between the internal elements of FIG. 4.

Referring to FIGS. 1-5, the measurement unit 120 disposed in the rear side of the pendant may be in continuous contact with the body of the user and may measure electrocardiogram or electromyogram. A signal measured by the measurement unit 120 may be an analog signal. The IC chip 132, as a signal processing unit, receives the analog signal from the measurement unit 120 and may process the received signal to transmit to an external apparatus or server. Generally, the IC chip 132 may amplify, filter, and convert the measured signal into a digital signal, and the processed signal may be transmitted to an external apparatus or server via the wireless communication unit 140.

In the present embodiment, it is described that the accessory 100 measures a biosignal and transmits the biosignal to the external apparatus or server. However, the accessory 100 may receive emergency information from the external apparatus or server and may display the degree of the danger for giving a warning to the user. Namely, the wireless communication unit 140 may include not only a function of transmission but also a function of reception.

Figure 6:
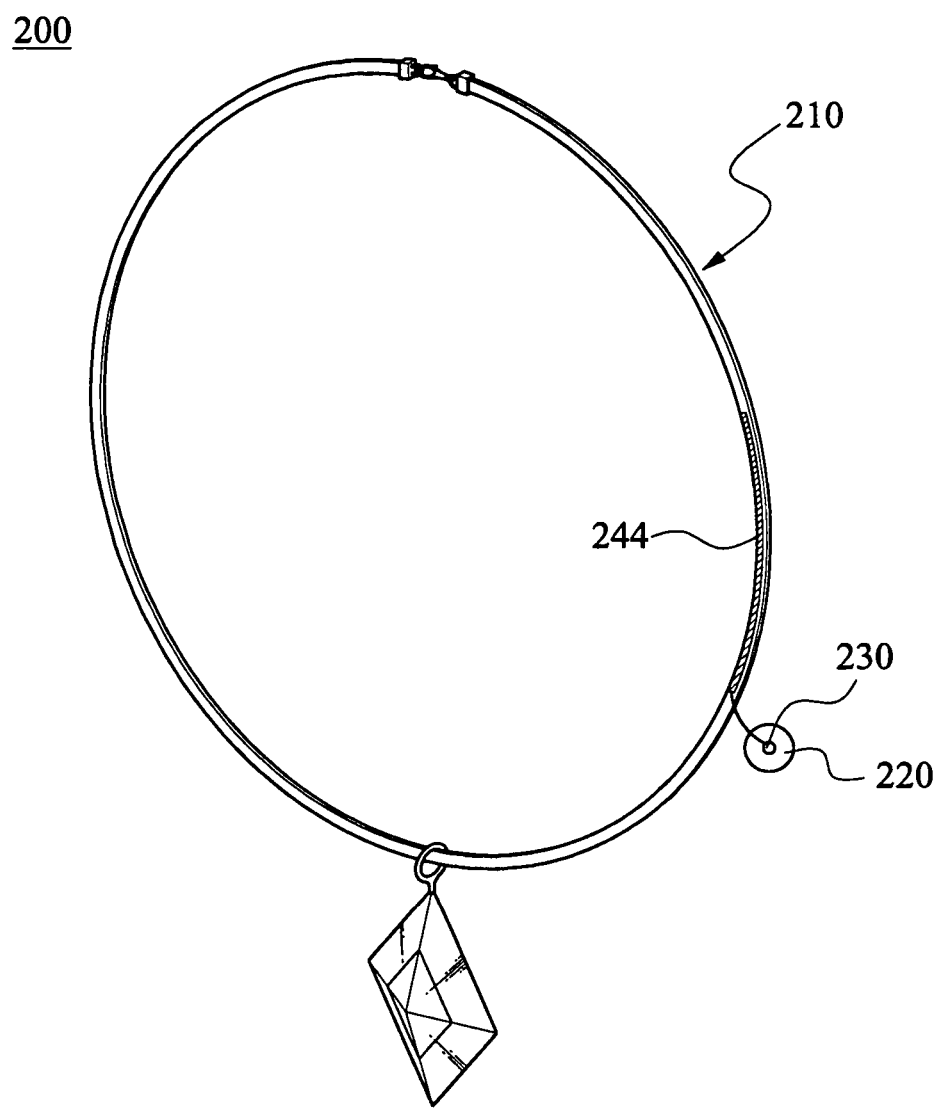
FIG. 6 is a perspective view illustrating an accessory according to another embodiment of the present invention.

FIG. 6 is a perspective view illustrating an accessory 200 according to another embodiment of the present invention.

For reference, the accessory 200 of FIG. 6 is a necklace but includes a measurement unit and a ground mounted separately from a pendant.

Referring to FIG. 6, the accessory 200 includes an accessory body 210 formed in the shape of a necklace, a measurement unit 220 provided on the side of a string of a necklace and in contact with a body of a user, a signal processing unit 230 mounted on the measurement unit 220, and a ground 244. The measurement unit 220 is formed in the shape of a disk, as a conventional sensing electrode for medical use. An electrode in contact with the user's body is included underneath the measurement unit 220.

The signal processing unit 230 is mounted on the top of the measurement unit 220 and includes an IC chip including a signal processing circuit and a monopole antenna. The IC chip of the signal processing unit 230 measures, converts, and processes a biosignal. The IC chip is electrically connected to the electrode of the measurement unit 220. Also, the monopole antenna of the signal processing unit 230 is functionally connected to the ground 244.

The measurement unit 220 and the signal processing unit 230 are installed in a part of the string of the accessory body 210, and the ground 244 in the body. Though the measurement unit 120 and the PCB substrate 130 are built into the accessory body 110 in FIGS. 1 and 2, in the present embodiment, the measurement unit 220 and the signal processing unit 230 are formed on the outside of the accessory body 210 and the ground 244 is wired by using the string.

The ground 244 is formed in a length greater than approximately $\lambda/4$ of a used frequency. Accordingly, the IC chip of the signal processing unit 230 may form a wireless communication unit by using the monopole antenna and the ground 244, and the ground 244 may function as a valid image antenna with respect to the monopole antenna.

The measurement unit 220 mounted on the string may receive a signal for monitoring a biosignal of a user by being in contact with the user's body. As described above, the biosignal may include an electrocardiogram (ECG), an electromyogram (EMG), an electroencephalogram (EEG), a galvanic skin response (GSR), a body temperature, a pulse, and a blood pressure.

In the present embodiment, one measurement unit 220 is mounted on the string, but the type or number of measurement units may vary. When a plurality of measurement units is formed, the measurement units may be independent or may be dependently connected to each other along the string.

The measurement 220 may measure an ECG or an EMG while being in contact with the user's body. The signals measured by the measurement unit 220 may be prepared to be transmitted externally via the IC chip of the signal processing unit 230. The IC chip may amplify, filter, and convert the measured signal into a digital signal to transmit to an external apparatus or server via a wireless communication unit.

FIG. 7 is a perspective view illustrating an accessory 300 according to still another embodiment of the present invention.

Referring to FIG. 7, the accessory 300 is a watch and includes an accessory body 310 in the shape of a watch, a measurement unit 320 mounted on a part of the accessory body 310 and in contact with a user's wrist, a signal processing unit 330 including an IC chip including a signal processing circuit, a monopole antenna (not shown), and a ground 344.

The accessory body 310 includes a watch body and a watch band 314. The measurement unit 320 capable of being in contact with the wrist is installed in the bottom of the watch body, and the signal processing unit 330 including the IC chip is formed in a watch body together with the measurement unit 320. Also, the signal processing unit 330 includes the IC chip and the monopole antenna on a single PCB substrate. Since internal elements of the accessory have been previously described with reference to FIG. 4, detailed configuration and description will be omitted.

Referring to FIG. 7, both sides of the watch body are connected to the watch band 314, and the monopole antenna and the ground 344 are electrically connected to a portion of the connection between the watch body and the watch band 314. The ground 344 is built in the watch band 314 and formed in a length of at least more than approximately $\lambda/4$ of a used frequency. Accordingly, the IC chip may form a wireless communication unit by using the monopole antenna and the ground 344, and the ground 344 may function as a valid image antenna with respect to the monopole antenna.

The measurement unit 320 mounted on the watch body may receive a signal for monitoring a biosignal of a user while being in contact with the user's wrist. Generally, the biosignal may include an ECG, an EMG, an EEG, a GSR, a body temperature, a pulse, and a blood pressure. In addition, the measurement unit may sense a temperature, a pressure, a humidity, a components of air, a composition of air, a radioactivity, and a deleterious bacteria of the surrounding environment.

In the present embodiment, the measurement unit 320 includes one contact terminal, but according to the type and number of biosignals to be measured, two or more contact terminal may be provided and a position of the contact terminal may be determined.

The measurement unit 320 in the rear of the watch body may measure an ECG or an EMG while being in contact with the user's wrist. A signal measured by the measurement unit 320 is an analog signal. The IC chip of the signal processing unit 330 receives the analog signal from the measurement unit 320 and may prepare to transmit the received signal outside by processing. The IC chip may amplify, filter, and convert the measured signal into a digital signal, and the processed signal may be transmitted to an external apparatus or server via a wireless communication unit.

FIG. 8 is a perspective view illustrating an accessory 400 according to yet another embodiment of the present invention.

Referring to FIG. 8, the accessory 400 is motivated by glasses and includes an accessory body 410 in the shape of glasses, a measurement unit 420 mounted on a part of the accessory body 410 and in contact with sides of a user's head, a signal processing unit 430 including an IC chip including a signal processing circuit, a monopole antenna (not shown) and a ground 444 mounted together with the IC chip on a substrate.

The accessory body 410 includes a glasses body and glasses legs (or temples) 414 formed on both ends of the glasses body. The measurement unit 420 capable of being in contact with a side of a face is installed in one of the glasses legs 414. The signal processing unit 430 including the IC chip is installed in the glasses leg 414, close to the measurement unit 420. Also, the signal processing unit 430 includes the IC chip and the monopole antenna on a single PCB substrate.

The measurement unit 420, the signal processing unit 430, and the ground 444 are sequentially provided along the glasses leg 414. The ground 444 is built in the glasses leg 414 and formed in a length greater than approximately $\lambda/4$ of a used frequency. Accordingly, the IC chip may form a wireless communication unit by using the monopole antenna and the ground 444, and the ground 444 may function as a valid image antenna with respect to the monopole antenna.

The measurement unit 420 mounted on the glasses leg 414 may receive signals associated with an ECG, an EMG, an EEG, a GSR, a body temperature, a pulse, and a blood pressure of a user while being in contact with the head. Though the measurement unit 420 is mounted in one of the glasses legs 414 in the present embodiment, according to the type and number of biosignals to be measured, two or more measurement units may be provided in each glasses leg.

The measurement unit 420 in the glasses leg 414 may measure a desired biosignal while being in contact with the head. A signal measured by the measurement unit 420 is processed via the IC chip of the signal processing unit 430, and the processed signal may be transmitted to an external apparatus or server by using the monopole antenna and the ground 444.

The accessories of the above-described embodiments of the present invention may be conventional accessories or small articles and may include a micro circuit unit and an antenna. However, since a ground has to have a certain length for effective communication, the ground may be built or wired into an accessory body in the certain length. A ground having more than the certain length makes an efficient wireless communication of the accessory possible.

Since the shapes of conventional clothing articles or accessory can be used as an accessory body of the present invention, it is simple to put on or carry, thereby maximizing convenience of users.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

What is claimed is:

1. An accessory for remote monitoring, comprising:
a body capable of being placed on a monitored subject;
a measurement unit provided on the body to be in contact with the subject to measure at least one biosignal of the subject;
a signal processing unit to process a signal acquired from the measurement unit; and
a wireless communication unit including a monopole antenna to transmit the signal processed by the signal processing unit, and a ground installed in the body corresponding to the monopole antenna,
wherein the signal processing unit and the monopole antenna are provided on the body and electrically connected to the measurement unit provided on the body,
wherein the ground functions as a valid image antenna with respect to the monopole antenna,
wherein the ground is installed in the body to form a part of the body,
wherein the body has a strip to be hanged on the subject, and
wherein the ground electrically connected to the monopole antenna is built in the strip, and a length of the ground is greater than approximately $\lambda/4$ of a frequency used by the wireless communication unit to transmit the signal processed by the signal processing unit.

2. The accessory of claim 1, wherein the body is in a form of a necklace, a bracelet, a belt, a watch, a band, a ring, or a pair of glasses.

3. The accessory of claim 2, wherein the ground is in the body along a periphery of the body.

4. The accessory of claim 1, wherein the measurement unit measures at least one of an electrocardiogram, an electromyogram, an electroencephalogram, a galvanic skin response, an electrooculogram, a body temperature, a pulse, a blood pressure, and a physical movement.

5. The accessory of claim 1, wherein the signal processing unit is in an integrated circuit (IC) chip on a printed circuit (PCB) substrate.

6. The accessory of claim 5, wherein the monopole antenna is on the PCB.

7. The accessory of claim 1, wherein the wireless communication unit also receives information.

8. The accessory of claim 1, wherein the monopole antenna is functionally connected to the ground.

9. An accessory for remote monitoring, comprising:
a body capable of being placed on a monitored subject;
a measurement unit provided on the body to be in contact with the subject to measure at least one biosignal of the subject;
a circuit unit including an integrated circuit chip to process a signal acquired from the measurement unit and a monopole antenna formed on the same substrate on which the integrated circuit chip is installed; and
a ground connected to the circuit unit and extended in the body, and the ground functions as a valid image antenna with respect to the monopole antenna,
wherein the circuit unit and the monopole antenna are provided on the body and electrically connected to the measurement unit provided on the body,
wherein the ground is installed in the body to form a part of the body,
wherein the body has a strip to be hanged on the subject, and
wherein the ground electrically connected to the monopole antenna is built in the strip, and a length of the ground is greater than approximately $\lambda/4$ of a frequency used by the wireless communication unit to transmit the signal processed by the signal processing unit.

10. The accessory of claim 9, wherein the body is in a form of a necklace, a bracelet, a belt, a watch, a band, a ring, and a pair of glasses.

11. The accessory of claim 9, wherein the measurement unit measures at least one of an electrocardiogram, an electromyogram, an electroencephalogram, a galvanic skin response, an electrooculogram, a body temperature, a pulse, a blood pressure, and a physical movement.

12. A method of remote monitoring, comprising:
placing a body on a monitored subject;
measuring at least one biosignal of the object subject via a measurement unit provided on the body to be in contact with the subject ;
processing, via a signal processing unit, a signal acquired from the measurement unit; and
transmitting the signal processed by the signal processing unit via a wireless communication unit including a monopole antenna, and a ground installed in the body corresponding to the monopole antenna and functioning as a valid image antenna with respect to the monopole antenna,
wherein the signal processing unit and the monopole antenna are provided on the body and electrically connected to the measurement unit provided on the body,
wherein the ground is installed in the body to form a part of the body,
wherein the body has a strip to be hanged on the subject, and
wherein the ground electrically connected to the monopole antenna is built in the strip, and a length of the ground is greater than approximately $\lambda/4$ of a frequency used by the wireless communication unit to transmit the signal processed by the signal processing unit.

* * * * *